United States Patent [19]

Klitgaard et al.

[11] Patent Number: 4,685,465

[45] Date of Patent: Aug. 11, 1987

[54] ELECTRODE DEVICE FOR TRANSCUTANEOUSLY MEASURING A BLOOD GAS PARAMETER AND FOR SENSING A BIOELECTRICAL SIGNAL AND AN ELECTRODE ASSEMBLY COMPRISING SUCH AN ELECTRODE DEVICE

[75] Inventors: Peter C. Klitgaard, Virum; Knud G. Pedersen, Lyngby, both of Denmark

[73] Assignee: Radiometer A/S, Copenhagen NV, Denmark

[21] Appl. No.: 709,027

[22] PCT Filed: May 24, 1984

[86] PCT No.: PCT/DK84/00048

§ 371 Date: Jan. 24, 1985

§ 102(e) Date: Jan. 24, 1985

[87] PCT Pub. No.: WO84/04815

PCT Pub. Date: Dec. 6, 1984

[30] Foreign Application Priority Data

May 24, 1983 [DK] Denmark .............................. 2301/83

[51] Int. Cl.[4] .......................... A61B 5/00; A61B 5/04
[52] U.S. Cl. .................................... 128/635; 128/640; 204/403; 204/415
[58] Field of Search ................ 128/635, 639–643; 204/403, 415, 431, 433

[56] References Cited

U.S. PATENT DOCUMENTS

| 4,252,124 | 2/1981 | Maurer et al. | 128/635 |
|---|---|---|---|
| 4,281,659 | 8/1981 | Farrar et al. | 128/635 |
| 4,294,258 | 10/1981 | Bernard | 128/635 |
| 4,320,764 | 3/1982 | Hon | 128/635 |
| 4,517,982 | 5/1985 | Shiga et al. | 128/635 |
| 4,538,617 | 9/1985 | Jensen | 128/635 |

FOREIGN PATENT DOCUMENTS

| 0139895 | 5/1979 | Denmark. | |
|---|---|---|---|
| 071980 | 2/1983 | European Pat. Off. | |
| 077054 | 4/1983 | European Pat. Off. | |
| 2930663 | 2/1981 | Fed. Rep. of Germany | 128/635 |
| 0152208 | 11/1981 | Fed. Rep. of Germany | 204/403 |
| 1402205 | 8/1975 | United Kingdom. | |

OTHER PUBLICATIONS

Journal of Perinatal Medicine 1 (1973) pp. 183–191. R. Huch et al, "Transcutaneous Measurement of Blood $Po_2$ ($tcPo_2$)—Method and Application in Perinatal Medicine."

*Primary Examiner*—Lee S. Cohen
*Attorney, Agent, or Firm*—Stiefel, Gross, Kurland & Pavane

[57] ABSTRACT

An electrode device for transcutaneously measuring the blood gas parameter and for sensing a bioelectrical signal and an electrode assembly comprising such an electrode device are disclosed. The electrode assembly for transcutaneously measuring a blood gas parameter and for measuring a bioelectrical signal comprises two separate electrode devices one of which further comprises an electrochemical measuring electrode system. The electrochemical measuring electrode system comprises a reference electrode of a potentiometric electrode system and an anode of a polarographic electrode system constituted by a single metallic body, a pH-electrode of the potentiometric electrode system, and a noble metal cathode of the polarographic electrode system. By means of the electrode assembly, coincident measurement of the blood gas partial pressures of oxygen and carbon dioxide and of a bioelectrical signal such as the ECG (Electrocardiography), the RR (Respiration rate) or the heart rate of the test person or patient is obtainable.

21 Claims, 8 Drawing Figures

ELECTRODE DEVICE FOR TRANSCUTANEOUSLY MEASURING A BLOOD GAS PARAMETER AND FOR SENSING A BIOELECTRICAL SIGNAL AND AN ELECTRODE ASSEMBLY COMPRISING SUCH AN ELECTRODE DEVICE

The present invention relates to an electrode device for transcutaneously measuring a blood gas parameter and for sensing a bioelectrical signal.

BACKGROUND OF THE INVENTION

The technique of transcutaneously measuring a blood gas parameter by arranging an electrochemical measuring electrode device on a skin surface part of a test person or a patient, is well-known in the art. The measurement is conventionally carried out in accordance with well-known measuring principles, such as the polarographic measuring principle or the potentiometric measuring principle.

In accordance with the potentiometric measuring principle, the blood gas parameter to be measured is the partial pressure of a gas which in an aqueous solution generates an acid or a base. Conventionally, an electrochemical measuring electrode device is employed which, in accordance with the Stow-Severinghaus principle, comprises a potentiometric electrode system including a pH-electrode and a reference electrode, and an electrolyte solution which communicates with the electrode system.

Correspondingly, in accordance with the polarographic measuring principle, the blood gas parameter to be measured is the partial pressure of oxygen. Conventionally, an electrochemical measuring electrode device is employed which, in accordance with the Clark measuring principle, comprises a polarographic electrode system including a cathode and an anode, and an electrolyte solution which communicates with the electrode system.

In operation of a Stow-Severinghaus electrode device for potentiometrically measuring the partial pressure of gas which in an aqueous solution generates an acid or a base, especially carbon dioxide, the gas in question permeates into the electrolyte solution and is dissolved therein, thereby causing a shift of pH, e.g.:

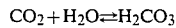

$$CO_2 + H_2O \rightleftharpoons H_2CO_3$$

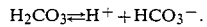

$$H_2CO_3 \rightleftharpoons H^+ + HCO_3^-.$$

Correspondingly, in operation of a Clark electrode device, e.g. when measuring the partial pressure of $O_2$, the gas to be measured permeates into the electrolyte solution and is reduced at the cathode, i.e. the gas in question is consumed by the polarographic electrode system, i.e.:

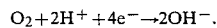

$$O_2 + 2H^+ + 4e^- \rightarrow 2OH^-.$$

Furthermore, the technique of sensing a bioelectrical signal is well-known in the art. Conventionally, the bioelectrical signal is sensed by means of two or more electrodes which are arranged in contact with respective skin surface parts of the test person or patient and by detecting the voltage variation across the bioelectrical signal sensing electrodes. The bioelectrical signal normally represents the respiration rate, the heart rate, the ECG (Electrocardiography), or the EEG (Electroencephalography) of the test person or the patient.

Since a very important and extensive application of the electrochemical measuring electrode devices for transcutaneously measuring a blood gas parameter and of the bioelectrical signal sensing electrodes is the supervision of newborn or even prematurely born infants, there has been a need for extremely small, compact and light-weight constructions of electrochemical measuring electrode devices and of bioelectrical signal sensing electrodes, yet providing extremely reliable and accurate measuring results as to the blood gas parameter to be measured and the bioelectrical signal to be sensed, respectively. In an attempt to obtain an even higher degree of compactness it has been suggested to arrange an electrochemical measuring electrode device and a bioelectrical signal sensing electrode in a single housing, vide e.g. German patent specification DE-OS No. 29 30 663, however comprising separate electrochemical measuring components and bioelectrical signal sensing components.

Furthermore, it has been suggested to employ an electrochemical measuring electrode device comprising a separate metal component of an annular configuration surrounding the electrodes and serving the purpose of thermostatically heating the skin surface part of the test person or patient and further serving as a bioelectrical signal sensing electrode, vide e.g. published European patent application, publication number 0 071 980. Whereas the above integrally housed electrochemical measuring electrode device and bioelectrical signal sensing electrode to no substantial extent provide a reduction of the overall size and weight of the transcutaneously, blood gas parameter measuring and bioelectrical signal sensing equipment to be arranged on a newborn or prematurely born infant, as the total number of components and the size thereof is basically identical to the total number of components of identical size of a discrete electrochemical measuring electrode device and of a discrete bioelectrical signal sensing electrode, the above combined construction, in which the separate metal component is employed as the bioelectrical sensing electrode, suffers from an inherent conflict, as, on the one hand, the separate metal component has to be arranged in intimate contact with the skin surface part of the person or patient to be supervised in order to provide maximum transmission of heat from the thermostatically heated metal component to the skin surface part, and, on the other hand, the bioelectrical signal sensing electrode, as is well known in the art, preferably is arranged recessed in relation to the skin surface part of the patient in order to make the bioelectrical signal sensing procedure less sensitive to incidental motions of the patient as is described in reference 1.

Therefore, there is a need for an electrode device for transcutaneously measuring a blood gas parameter and for sensing a bioelectrical signal, which electrode device provides a mroe compact and lightweight construction than an assembly of a discrete, electrochemical measuring electrode device and a discrete, bioelectrical signal sensing electrode without introducing limitations as to its measuring accuracy and measuring reliability as compared to the discrete, electrochemical measuring electrode device and the discrete bioelectrical signal sensing electrodes.

SUMMARY OF THE INVENTION

This need is fulfilled by means of an electrode device according to the invention for transcutaneously measuring a blood gas parameter and for sensing a bioelectrical signal, comprising:
- a housing having a front surface adapted to be arranged in contact with a skin surface part of a test person or a test object,
- an electrochemical measuring electrode system for measuring said blood gas parameter and comprising:
  - at least two electrochemical electrodes, the electrochemical electrodes being arranged in the housing electrically insulated in relation to one another, and
  - an electrolyte solution, the electrolyte solution being arranged electrolytically communicating with the electrodes and covering at least a part thereof,
- and an electrode for sensing said bioelectrical signal, the bioelectrical signal sensing electrode being constituted by one of the electrodes of the electrochemical electrode system, the said one electrode being adapted to electrically conductively communicate with the skin surface part when the front surface of the electrode device housing is arranged in contact therewith. In accordance with the teaching of the present invention, it is rendered possible to combine the bioelectrical signal sensing electrode and one of the electrodes of the electrochemical electrode system into a single electrode, thus providing a more compact construction of the electrode device.

In accordance with the presently preferred embodiment of the electrode device according to the invention, the said one electrode has a first part and a second part, the first part being covered by the electrolyte solution and electrolytically communicating therewith, and the second part being uncovered by the electrolyte solution and adapted to electrically conductively communicate with the skin surface part when the front surface of the electrode device housing is arranged in contact therewith. By providing separate first and second parts of the electrode constituting the bioelectrical signal sensing electrode and one of the electrodes of the electrochemical electrode system and communicating electrically conductively with the skin surface part and electrolytically with the electrolyte solution, respectively, the electrochemical measuring electrode system and the bioelectrical signal sensing electrode do not substantially influence one another.

In the presently preferred embodiment of the electrode device comprising separate first and second parts of the combined electrode, the first part and the second part of the said one electrode are separated from one another by a membrane permeable to the blood gas, the membrane being arranged in front of the electrodes and defining an electrolyte solution chamber in front of the electrodes, in which chamber the electrolyte solution is confined. By providing a separation membrane, the separation between the first and second parts of the combined electrode is increased, and, consequently, the influence from the electrochemical measuring electrode system and the bioelectrical signal sensing electrode on one another is further reduced.

In the embodiment of the electrode device according to the invention comprising a first and a second part of the combined electrode, the second part thereof may be adapted to electrically conductively communicate with the skin surface part through a direct contact with the skin surface part or actually through a perspiration layer, when the front surface of the electrode device is arranged in contact with the said skin surface part. However, it is preferred that the second part of the said one electrode is adapted to electrically conductively communicate with the skin surface part through an electrically conductive contact liquid when the front surface of the electrode device housing is arranged in contact therewith, as a more reliable, electrical contact is established, which is independent of the humidity of the skin surface part, the actual contact pressure, etc, as is well known in the art.

By providing a second part adapted to electrically conductively communicate with the skin surface part through an electrically conductive contact liquid, it is further rendered possible to provide an embodiment of the electrode device according to the invention in which embodiment the second part of the said one electrode is recessed in relation to the front surface of the electrode device housing, which further reduces the sensitivity of the bioelectrical signal sensing electrode to incidental motions of the test person or patient.

The electrochemical measuring electrode system may be adapted to measure any blood gas parameter. However, the blood gas parameter is conventionally the blood gas partial pressure of carbon dioxide or oxygen. Consequently, in accordance with a first embodiment of the electrode device according to the invention the electrochemical measuring electrode system is adapted to measure the blood gas partial pressure of carbon dioxide or any other constituent which in an aqueous solution generates an acid or a base and comprises a potentiometric electrode system including a reference electrode and a pH-sensitive electrode, the reference electrode further constituting the bioelectrical signal measuring electrode.

In this embodiment of the invention, the reference electrode is preferably a silver reference electrode, and the pH-sensitive electrode is a pH-glass electrode.

In a second embodiment of the electrode device according to the invention, the electrochemical measuring electrode system is adapted to measure the blood gas partial pressure of oxygen and comprises a polarographic sensing electrode system including a cathode and an anode, the anode further constituting the bioelectrical signal sensing electrode.

In accordance with the embodiment of the invention, the anode is preferably a silver anode, and the cathode is a noble metal cathode, such as a gold or preferably a platinum cathode further constituting the bioelectrical signal sensing electrode.

In accordance with the teaching of the present invention, it is rendered possible to provide a combined electrode device for transcutaneously measuring the partial pressures of oxygen and carbon dioxide and for sensing a bioelectrical signal comprising a potentiometric electrode system and a polarographic measuring electrode system in which the reference electrode of the potentiometric electrode system and the anode of the polarographic electrode system are constituted by a single electrode further constituting the bioeelectrical signal sensing electrode.

In the combined oxygen and carbon dioxide measuring and bioelectrical signal sensing electrode device according to the invention, the said single electrode is preferably a silver electrode.

In the presently preferred embodiment of the combined oxygen and carbon dioxide measuring and bioelectrical signal sensing electrode device according to the invention, the silver electrode is constituted by a silver body in which the pH-electrode of the potentiometric electrode system and the cathode of the polarographic electrode system are embedded.

The electrode device according to the invention may further comprise thermostating means for thermostatically controlled heating of the device to a predetermined temperature above the normal skin temperature in order to obtain hyperaemia. In the above described combined $O_2$ and $CO_2$ measuring and bioelectrical signal sensing electrode device according to the invention comprising a silver body, the thermostating means are preferably embedded in the silver body in thermally conductive contact therewith.

In accordance with the teachings of the presenet invention, it is rendered possible to provide an electrode device further comprising a second bioelectrical signal sensing electrode, the second bioelectrical signal sensing electrode being constituted by a separate metallic body, the separate metallic body being electrically insulated in relation to the said one electrode and having an exposed surface part. Consequently, an electrode device comprising two separate, mutually insulated bioelectrical signal sensing electrodes, together constituting a bioelectrical signal measuring system, is provided.

A very important application of the electrode device comprising an electrochemical measuring electrode system and further comprising a bioelectrical signal measuring system is the parturition supervision by which the separate metallic body constituting the second bioelectrical signal sensing electrode is electrically conductively connected to the skin surface through different body liquids, such as amniotic fluid, blood, etc. In accordance with the presently preferred embodiment of the electrode device comprising an electrochemical measuring electrode system and further a bioelectrical signal measuring system, the metallic body constituting the second bioelectrical signal sensing electrode is a part of the electrode device housing.

In order to render it possible to arrange and maintain the front surface of the electrode device housing in contact with the skin surface part, the electrode device according to the invention may advantageously further comprise a fastening means for fastening the electrode device to said skin surface part. The fastening means of the electrode device may be constituted by any appropriate means serving the purpose of maintaining the electrode device in a predetermined position relative to the skin surface. In the presently preferred embodiment of the electrode device according to the invention, the fastening means is a separate fastening component, basically of the type described in U.S. Pat. No. 4,274,418, of an annular configuration, the fastening component being adapted to receive the housing of the electrode device, and, together with the front surface of the electrode device, define a contact liquid chamber, in which the electrically conductive contact liquid, which serves the purpose of providing electrically conductive communication between the said one electrode and the skin surface part, is confined when the housing of the electrode device is received in the annular fastening component.

The present invention further relates to an electrode assembly for transcutaneously measuring a blood gas parameter and for measuring a bioelectrical signal comprising:
an electrode assembly for transcutaneously measuring a blood gas parameter and for measuring a bioelectrical signal, comprising:
  a first electrode device comprising:
    a housing having a front surface adapted to be arranged in contact with a first skin surface part of a test person or a test object,
    an electrochemical measuring electrode system for measuring said blood gas parameter and comprising:
      at least two electrochemical electrodes, the electrochemical electrodes being arranged in the housing electrically insulated in relation to one another, and
      an electrolyte solution, the electrolyte solution being arranged electrolytically communicating with the electrodes and covering at least a part thereof,
    and an electrode for sensing said bioelectrical signal, said bioelectrical signal sensing electrode being constituted by one of the electrodes of the electrochemical electrode system the said one electrode being adapted to electrically conductively communicate with said first skin surface part when the front surface of the first electrode device housing is arranged in contact therewith,
  and a second electrode device comprising:
    a housing having a front surface adapted to be arranged in contact with a second skin surface part of a test person or a test object, and
    an electrode for sensing said bioelectrical signal, the bioelectircal signal sensing electrode being adapted ot electrically conductively communicate with said second skin surface part when the front surface of the second electrode device housing is arranged in contact therewith,
  said first and second bioelectrical signal electrodes being adapted to cooperate with a measuring apparatus for measuring said bioelectrical signal.

The electrode assembly may have its first and second electrode devices connected to the measuring apparatus through individual connections. However, in order to provide an integrated electrode assembly having a single connection to the measuring apparatus, the electrode assembly according to the invention may further comprise a junction, the first electrode device and the second electrode device being connected to the junction for joint connection to the measuring apparatus.

In the electrode assembly according to the invention, which renders it possible to measure a blood gas parameter and to measure a bioelectrical signal, the first electrode device may have any of the above described characteristics, and the bioelectrical signal sensing electrode of the second electrode device may be adapted to electrically conductively communicate with said second skin surface part through an electrically conductive contact liquid when the front surface of the electrode device housing of the second electrode device is arranged in contact therewith, thus, providing the above described advantage of establishing a highly electrically conductive connection between the bioelectrical signal sensing electrode of the second electrode device and the second skin surface part. In order to reduce the sensitivity of the bioelectrical signal measuring electrode sytem to incidental motion of the test person or the patient, as described above, the bioelectrical signal sensing electrode of the second electrode device is preferably recessed in relation to the front surface of the the second electrode device housing.

In accordance with the presently preferred embodiment of the electrode assembly according to the invention, the bioelectrical signal sensing electrode of the second electrode device is a silver electrode thus, in itself providing a highly conductive bioelectric signal sensing electrode.

In a further embodiment of the electrode assembly according to the invention, the second electrode device may further comprise a temperature sensing means, the temperature sensing means being adapted to thermally conductively communicate with the second skin surface part for sensing the temperature thereof, when the front surface of the second electrode housing is arranged in contact with the second skin surface part. Consequently, the electrode assembly according to the invention may sense or measure the skin surface temperature of the test person or patient, provide measurement of the partial pressures of oxygen and carbon dioxide, and measure a bioelectrical signal, such as the ECG (Electrocardiography), the HR (heart rate) or the RR (the respiration rate) of the test person or patient. Contrary to this, five discrete sensors or electrode devices have hitherto been employed for providing these measurements, viz. a temperature sensor, a first and a second ECG electrode, a polarographic electrode device for measuring the partial pressure of oxygen, and a potentiometric electrode device for measuring the partial pressure of carbon dioxide.

The second electrode device of the electrode assembly according to the invention may further comprise a fastening means for fastening the second electrode device to said second skin surface part in order to render it possible to arrange and maintain the bioelectrical signal sensing electrode of the second electrode device in a predetermined position relative to the second skin surface part.

In this embodiment of the invention, the fastening component of the second electrode device is preferably a separate fastening component of an annular configuration, the fastening component being adapted to receive the housing of the second electrode device and, together with the front surface of the second electrode device, define a contact liquid chamber, i.e. basically of a configuration identical to the configuration of the separate fastening component of the first electrode device. The separate fastening component of the first electrode device and the separate fastening component of the second electrode device may in accordance with a further embodiment of the electrode assembly according to the invention be adapted to further enable interchanging of the electrode devices in relation to the fastening components. By interchanging the positions of the first electrode device and the second electrode device of the electrode assembly, the risk of incurring to the test person or patient injuries caused by overheating the skin surface part which is in contact with the front surface of the first electrode device of the electrode assembly is reduced, as the first and the second electrode device of the electrode assembly may be interchanged, so that the thermostatically heated first electrode device is shifted from a first fastening component to a second fastening component and vice versa within predetermined periods of time, e.g. every 4 hours.

BRIEF DESCRIPTION OF THE DRAWINGS

The present invention will now be further described with reference to the drawings, wherein.

DETAILED DESCRIPTION OF THE DRAWINGS

Figure 1:
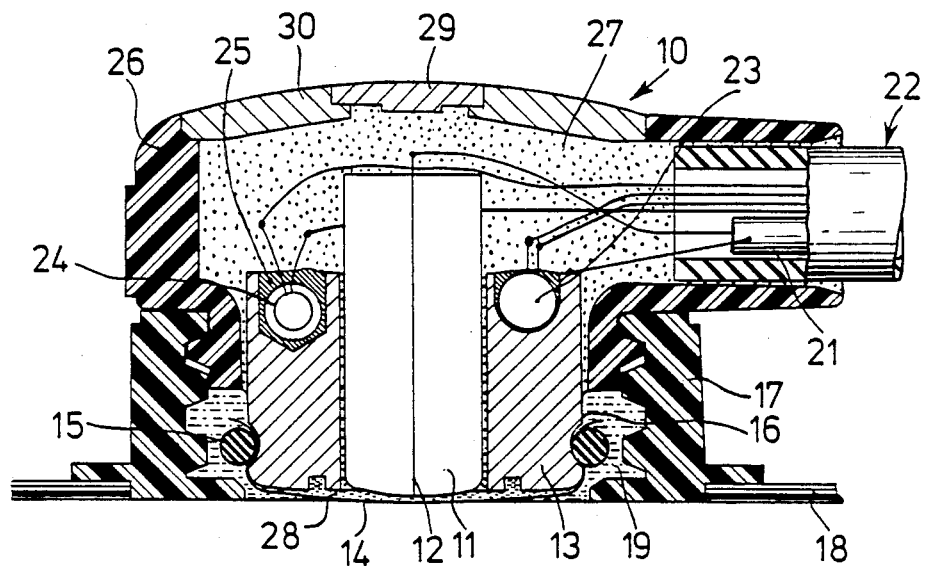
FIG. 1 is vertical, sectional view of a first embodiment of an electrode device according to the invention for transcutaneously measuring the blood gas partial pressure oxygen and for sensing a bioelectrical signal, FIG. 2 a partly sectional view of a second embodiment of an electrode device according to the invention for transcutaneously measuring the blood gas partial pressure of carbon dioxide and for sensing a bioelectrical signal, FIG. 3 a schematical and partly sectional view of an electrode assembly according to the invention for transcutaneously measuring the blood gas partial pressures of oxygen and carbon dioxide and for measuring a bioelectrical signal, FIG. 4 an overall diagram of a first embodiment of an electronic circuitry of a measuring apparatus cooperating with the electrode assembly shown in FIG. 3, FIG. 5 corresponding to FIG. 4 an overall diagram of a second embodiment of the electronic circuitry, FIG. 6 a diagram showing $pO_2$ and $pCO_2$ responses of the electrode device according to the invention constituting a first electrode device of the electrode assembly shown in FIG. 3, FIG. 7 a diagram showing ECG (electrocardiography) responses of the electrode assembly according to the invention, shown in FIG. 3, and of a conventional ECG electrode assembly, and FIG. 8 a diagram showing TTI (transthoracal impedance) variations obtained by means of the electrode assembly according to the invention shown in FIG. 3 and by means of the above mentioned conventional electrode assembly.

In FIG. 1, a first embodiment of an electrode device according to the invention for transcutaneously measuring the blood gas partial pressure of oxygen and for sensing a bioelectrical signal is shown designated the reference numeral 10 in its entity. The electrode device 10 comprises an electrochemical measuring electrode system including a noble metal cathode 12, preferably a platinum wire embedded in a glass tubing 11, and an anode constituted by a metallic body 13, preferably an Ag-body, in which the noble metal cathode wire embedding tubing 11 is centrally arranged. In front of the lower-side surface of the glass tubing 11 and the lower-side surface of the metallic body 13, an oxygen-permeable membrane 14 is arranged. The membrane 14 is maintained in a position relative to the anode and the cathode by means of an O-ring 15, which cooperates with an annular recess of the outer cylindrical surface of the metallic body 13. Within a chamber defined between the inner surface of the membrane 14 and the lower-side surface of the metallic body 13 and the tubing 11, an electrolyte solution 28 is encased.

Apart from the electrochemical measuring electrode system for measuring the blood gas partial pressure of oxygen, the electrode device 10 comprises an electrode for sensing a bioelectrical signal. Basically, the bioelectrical signal sensing electrode of the electrode device is constituted by the metallic body 13 also constituting the anode of the electrochemical measuring electrode system. However, the metallic body 13 is divided into two parts, a first part of the outer-side surface of the metallic body 13 being covered by the electrolyte solution 28 and further covered by the oxygen-permeable membrane 14, and a second part of the outer side surface of the metallic body 13 not being covered by the electrolyte solution. The second part of the metallic body 13 is designated the reference numeral 16. As is evident from FIG. 1, the electrode device 10 comprises an electrically insulating housing component 26, in which the metallic body 13 is partiall encased, and which is provided with an outer thread adapted to cooperate with a corresponding inner thread of an annular fixation ring 17, which is further adapted to cooperate with an annular adhesive ring 18. The annular adhesive ring 18 is at its lower-side surface provided with an adhesive layer, which serves the purpose of adhering to a skin surface part of a test person or patient, the oxygen blood gas partial pressure of whom is to be measured, and the bioelectrical signal of whom is to be sensed by means of the electrode device 10. As is evident from FIG. 1, an annular space defined between the inner-side surface of the fixation ring 17, the lower-side surface of the housing part 26, the uncovered or exposed outer-side surface 16 of the metallic body 13, the O-ring 15, and the outer-side surface of the oxygen-permeable membrane 14 is filled with an electrically conductive contact liquid 19, which serves the purpose of establishing electrically conductive communication or contact between the uncovered or exposed surface part 16 of the metallic body 13 and the skin surface part of the test person or patient. As is well-known in the art, the recessed configuration of the uncovered or exposed surface part 16 of the metallic body 13, actually the bioelectrical sensing electrode of the electrode device 10, provides diminished motion artifact or a reduced sensitivity of the bioelectrical signal electrode to incidental motion of the test person or patient, as described in reference 1.

The electrode device 10 further comprises thermostating means, which serve the purpose of heating the electrode device to a predetermined temperature above the normal skin termperature in order to establish hyperaemia at the skin surface part of the test person or patient to whom the electrode device is fixed. The thermostating means comprise a heating means and a temperature sensing means constituted by a Zener diode 23 and a NTC-resistor 24 respectively. The Zener diode 23 and the NTC-resistor 24 are cast into recesses of the metallic body 13 by means of respective thermally conductive castings, one of which is designated the reference numeral 25.

The individual means of the electrode device, i.e. the noble metal wire cathode 12, the metallic body 13 constituting the anode relative to the cathode and further constituting the bioelectrical signal sensing electrode, the Zener diode 23, and the NTC-resistor 24 are connected to external measuring and temperature controlling equipment, not shown in FIG. 1, through a multicore cable 22, a single insulated core of which is designated the reference numeral 21. The electrode device is further provided with two top surface housing parts 29 and 30 and the interior space defined within the electrode housing parts 26, 29 and 30 is filled with an electrically and thermally insulating casting 27.

In an alternative embodiment of the electrode device 10, shown in FIG. 1, the electrode housing parts 29 and 30 are made of a metal, such as stainless steel, together constituting a second bioelectrical signal sensing electrode of the electrode device. The second bioelectrical signal sensing electrode constituted by the metallic electrode housing parts 29 and 30 is connected to a single core of the multicore cable 22. This alternative embodiment of the electrode device is mainly adapted for parturition applications, in which the second bioelectrical sensing electrode is electrically conductively connected to the skin surface of the infant through different body liquids such as amniotic liquid, perspiration liquid, blood, etc. Basically, the second bioelectrical signal sensing electrode, constituted by the metallic electrode housing parts 29 and 30, constitutes a bioelectrical signal measuring electrode system together with the first bioelectrical signal sensing electrode, constituted by the metallic body 13 of the electrode device.

Figure 2:
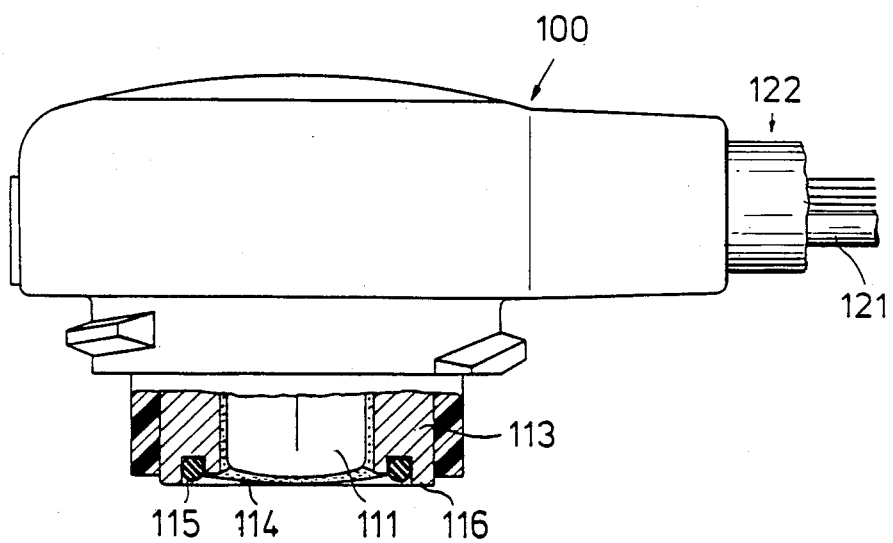

In FIG. 2, a second embodiment of an electrode device according to the invention for transcutaneously measuring the blood gas partial pressure of carbon dioxide and for sensing a bioelectrical signal is shown, designated the reference numeral 100 in its entity. The electrode device 100 basically differs from the electrode device 10, shown in FIG. 1, in that the electrode device comprises a pH-glass electrode 111, which communicates electrolytically with a reference electrode constituted by a metallic body 113, preferably an Ag-body, in which the pH-glass electrode is centrally arranged. In front of the lowerside surface of the pH-glass electrode 111 a carbon dioxide permeable membrane 114 is arranged confining an electrolyte solution within an electrolyte solution chamber in front of the lower side surface of the pH-glass electrode 111 and a first part of the metallic body 113. The membrane 114 is maintained in position relative to the pH-glass electrode and the first part of the metallic body 113, constituting a reference electrode relative thereto, by means of an O-ring 115, which is received in an annular recess of the lower-side surface of the metallic body 113. The metallic body 113 is further provided with a protruding, uncovered or exposed lower-side surface part 116, constituting a second part of the metallic body 113 or the bioelectrical signal sensing electrode of the electrode device. Whereas the bioelectrical signal sensing electrode constituted by the uncovered or exposed surface part 16 of the electrode device 10 shown in FIG. 1 is adapted to communicate electrically with the skin surface part of the test person or patient through the electrically conductive contact liquid 19, the electrode device 100 shown in FIG. 2 is adapted to have its uncovered or exposed surface part 116 arranged in intimate contact with the skin surface part of the test person or patient through an electrically conductive contact liquid flim. Basically, this intimate contact between the skin surface part and the bioelectrical signal sensing electrode makes the bioelectrical signal sensing more sensitive to incidental motion of the test person or patient, as the electrical contact between the uncovered or exposed surface part 116 and the skin surface part is highly influenced by motion or vibration of the electrode device relative to the skin surface part of the test person or patient. Like the electrode device 10 shown in FIG. 1, the electrode 100 shown in FIG. 2 is provided with a multi-core cable 122, a single, electrically insulated core of which is designated the reference numeral 121.

Figure 3:
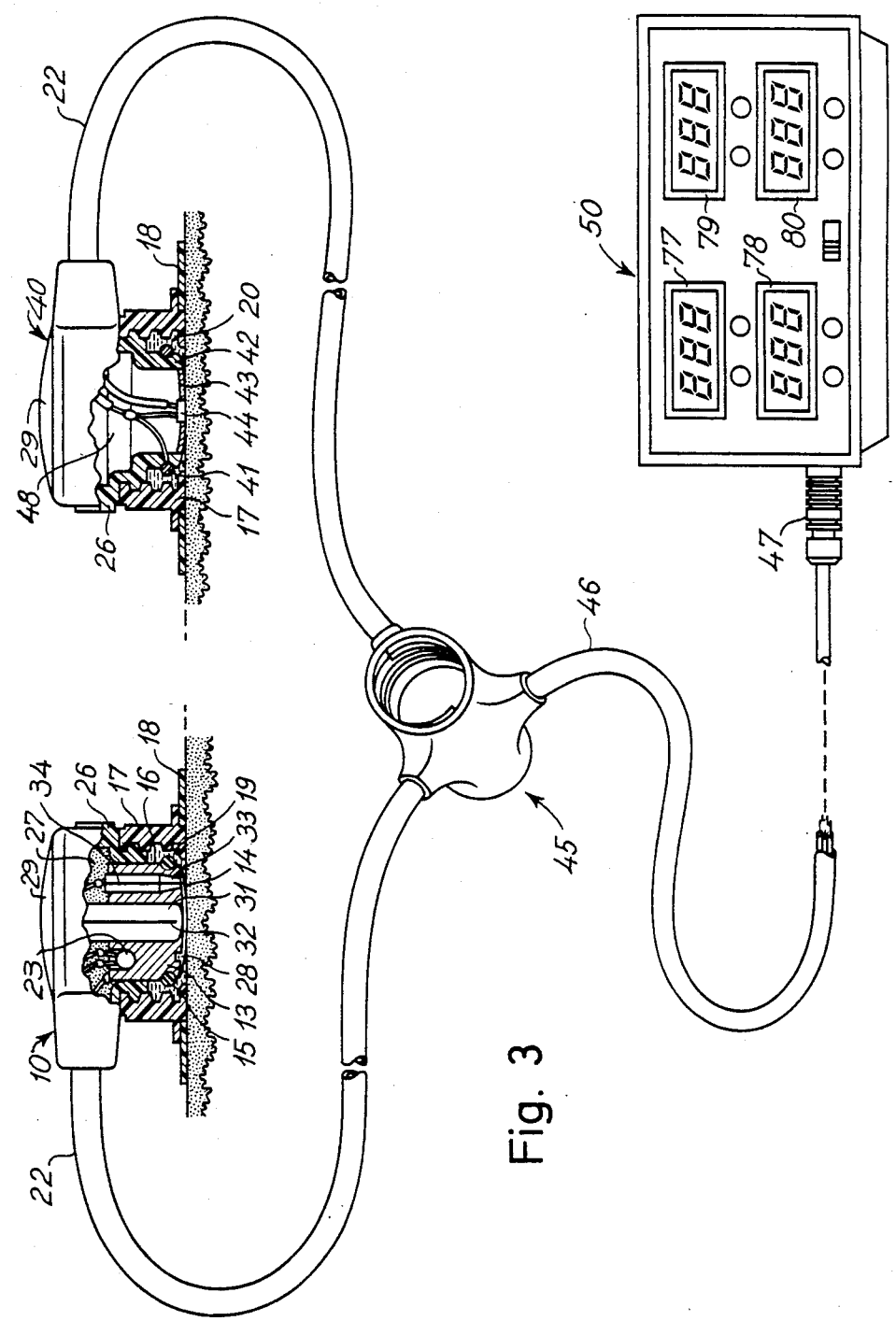

In FIG. 3, an electrode assembly according to the invention is shown comprising two electrode devices, one of which is basically identical to the electrode device designated 10 and described above with reference to FIG. 1. However, in the electrode device shown in the upper, left-hand side of FIG. 3, the central electrode corresponding to the noble metal cathode wire 12 embedded in the glass tubing 11 shown in FIG. 1 is a pH-electrode 31 comprising a main tube having a pH-sensitive glass membrane melted or otherwise fixed at the lower end thereof, and a central inner conductor 32. The electrode device 10 shown in FIG. 3 further comprises a cathode comprising a glass tubing 33 encasing a noble metal cathode wire 34. The metallic body 13, which is preferably an Ag-body, serves three purposes in the electrode device 10 shown in FIG. 3. First, the metallic body 13 constitutes a reference electrode relative to the central pH-glass electrode of the potentiometric electrode system; second, the metallic body 13 constitutes an anode relative to the cathode of the polarographic electrode system, and third, the metallic body 13 constitutes the bioelectrical signal sensing electrode of the electrode device in accordance with the principles of the present invention.

In the upper, right-hand side of FIG. 3, a second electrode device of the electrode assembly is shown. The electrode device 40 is basically of a configuration identical to the configuration of the electrode device 10. Thus, the electrode device 40 comprises housing and fixation ring components identical to the corresponding components of the electrode device 10. However, the electrode device 40 differs from the electrode device 10 in that it does not comprise any electrochemical electrode systems. The electrode device 40 comprises a bioelectrical signal sensing electrode, which is constituted by a metallic ring 41, preferably an Ag-ring, which is arranged in an outer peripheral recess of a housing part extension 42 of the housing part 26. Basically, the metallic ring 41 is arranged in a position on the electrode device 40 corresponding to the position of the O-ring on the electrode device 10. In the electrode device 10, the bioelectrical signal sensing ring electrode 41 is in electrically conductive connection or communication with the skin surface part through an electrically conductive contact liquid 20, which is confined within the interspace defined between the inner-side surface of the fixation ring 17 and the outerside surface of the metallic ring 41 and of the housing part extension 42 of the housing part 26. The inner space of the electrode device 40 is filled with air or filled with an electrically and thermally insulating casting.

In a central opening of the housing part extension 42 an electrically and thermally non-conductive part 43 is arranged. In a central bore of the part 43 a thermistor 44 is embedded. The thermistor 44 serves the purpose of providing an indication of intact or non-intact blood circulation in the tissue of the underlying skin surface part in accordance with the principles described in reference 2. The thermistor 44 is supplied with a predetermined amount of power for a predetermined period of time so that the thermistor supplies a predetermined amount of energy to the skin surface part, which is in contact with the electrode device. Thereafter, the temperature of the skin surface is measured and the temperature decay is monitored by means of the thermistor 44.

The multi-core cables 22 of the electrode devices 10 and 40 are connected to a common junction body 45. Basically, the junction body 45 is a tubular body having three protruding studs. At either end of the tubular body, the inner surface thereof is provided with an inner thread, one of which is shown in FIG. 1, and which are adapted to cooperate with the outer threads of the electrode housing parts 26 of the electrode devices 10 and 40 for receiving the electrode devices 10 and 40 in the tubular body when the electrode assembly is stored or transported so as to protect the highly delicate front surfaces of the electrode devices against mechanical damage. A multi-core cable 46 has its individual cores connected at its first end to the individual cores of the multi-core cables 22 of the electrode device 10 and of the electrode device 40 within the junction body 45. The multi-core cable 46 has its individual cores connected to individual pins of a multi-pin plug 47 at its other end. In FIG. 3, the multi-pin plug 47 is received in a cooperating connector socket of a measuring apparatus which is designated the reference numeral 50 in its entity. The measuring apparatus 50 is to be described in greater detail below with reference to FIGS. 4 and 5.

Figure 4:
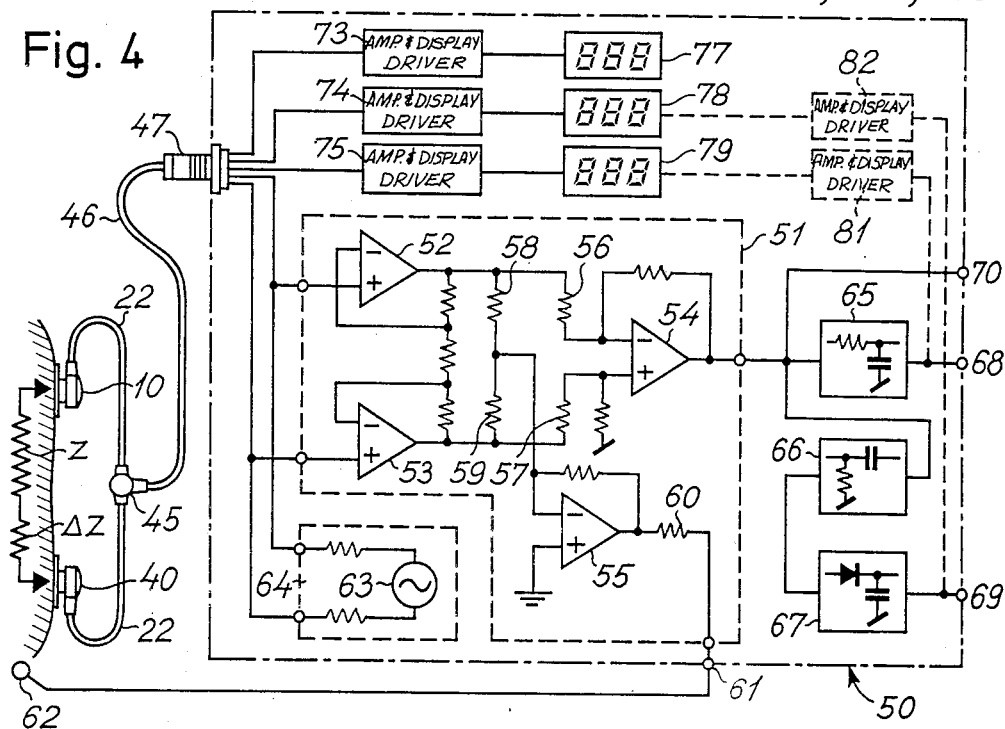
Figure 5:
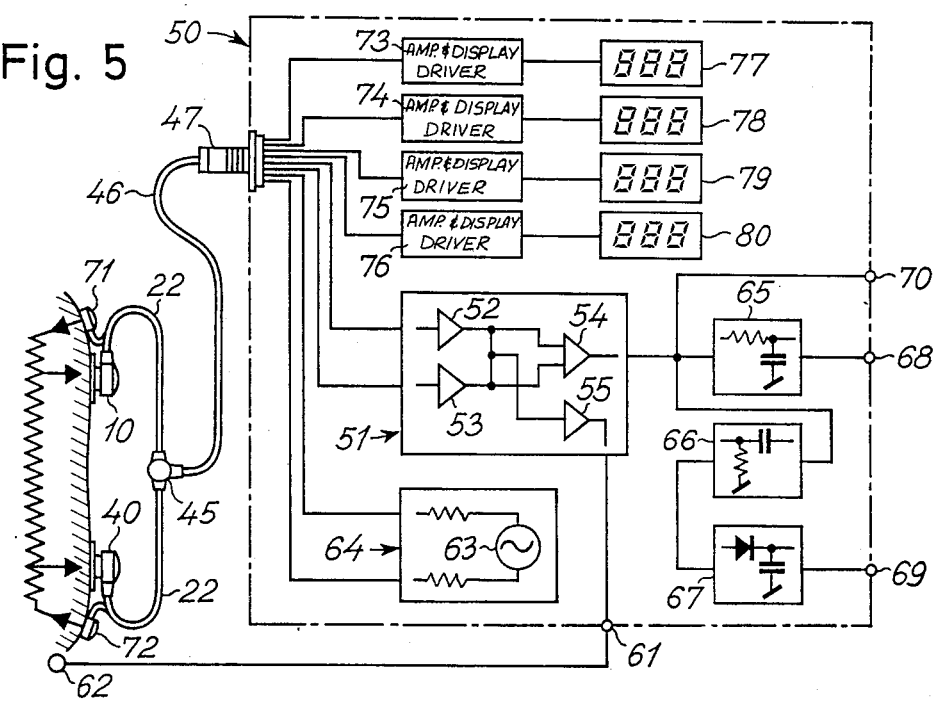

In FIGS. 4 and 5, the above described electrode assembly comprising the electrode devices 10 and 40 is shown together with a diagram of the electronic circuitry of the apparatus 50. Basically, the electronic circuitry configuration shown in FIG. 4 is a conventional differential amplifier implementation of an ECG (Electrocardiography), an HR (Heart rate) and an RR (Respiration rate) measuring apparatus. In a dotted line block 51 four operational amplifiers 52, 53, 54 and 55 are contained. The operational amplifiers 52 and 53 have their non-inverting inputs connected to a respective bioelectrical signal sensing electrode of a respective electrode device, i.e. one of the electrode devices 10 or 40, through individual cores of the multi-core cables 22 and 46. The operational amplifiers 52 and 53 are connected in a high-gain non-inverting mode and have their outputs connected to the inverting input and the non-inverting input of the operational amplifier 54 through resistors 56 and 57, respectively. Consequently, the operational amplifier 54 serves the purpose of generating a response at its output corresponding to the difference between the voltages originating from the operational amplifiers 52 and 53 and further from the respective bioelectrical signal electrodes of the electrode devices 10 and 40. The output of the operational amplifiers 52 and 53 are further connected to two resistors 58 and 59, which are identical to one another, and which have their common node connected to the inverting input of the operational amplifier 55. The operational amplifier 55, which is connected in a high-gain inverting mode, has its output connected through a resistor 60 to an output terminal 61 of the apparatus 50. The output terminal 61 is further connected to a bioelectrical signal reference electrode 62, which is only shown schematically. The apparatus 50 further comprises an AC constant current generator 63, which is included in a block 64, which is shown in dotted lines in FIG. 4. In FIG. 4, the AC generator 63 supplies current to one of the bioelectrical signal electrodes of the electrode assembly and through the thorax of the patient to the other bioelectrical signal sensing electrode of the electrode assembly. The impedance of the thorax is indicated as a two-component impedance comprising a fixed resistor Z and a varying resistor $\Delta Z$, which varies in accordance with the respiration rate of the patient or test person. As the above described AC generator 63 supplies current through the thorax of the test person or patient at a frequency of 20–100 kHz, preferably 80 kHz, the output of the operational amplifier 54, supplies an AM (amplitude modulated) signal to a high-pass filter block 66 and further to an AM demodulator 67, the output of which is connected to an output terminal 69. At the terminal 69, the high-pass filtered and demodulated TTI (transthoracal impedance) signal is available to external equipment, such as an oscilloscope or a frequency counter, which may provide the RR (respiration rate) by counting the peaks of the TTI signal. The output signal from the operational amplifier 54 is further present at a direct output terminal 70 of the apparatus 50 and is supplied to a low-pass filter block 65, which is connected to an output terminal 68. The signal at the output of the low-pass filter block, i.e. at the output terminal 68, represents a signal origin from bioelectrical signal sources within the test person or patient, i.e. the ECG (Electrocardiography). The output terminals 68 and 70 may be connected to appropriate external equipment, thus, the terminal 68 may be connected to an oscilloscope for displaying the ECG or to a frequency counter for providing the HR (heart rate) by counting the peaks of the ECG. The output terminal 70 may advantageously be connected to external data processing equipment such as an A/D (analogue/digital) converter for further supplying the measuring signal to signal processing or data processing equipment.

As described above with reference to FIG. 4, the AC generator 63 supplies its current to the bioelectrical signal sensing electrodes of the electrode assembly. Contrary to this, the AC generator 63 supplies, in FIG. 5, its current to individual or auxiliary current injection electrodes 71 and 72 through individual cores of the multi-core cables 46 and 22, and, consequently, independently relative to the signal sensing electrodes. By this separation of the current injection and the signal sensing, the sensitivity of the bioelectrical signal measuring system to incidental motion of the patient or test person is highly reduced.

In the apparatus 50 shown in FIG. 5, four amplifier and display driver blocks 73, 74, 75 and 76 are shown connected at their inputs to the polarographic electrode system, the potentiometric electrode system, the temperature sensor of the electrode device 10 and the thermistor of the electrode device 40, respectively, and at their outputs to displays 77, 78, 79 and 80, respectively, for displaying the partial pressure of oxygen, the partial pressure of carbon dioxide, the thermostating temperature and the estimated blood circulation, respectively. In the upper part of FIG. 4, only the blocks 73, 74 and 75 and the corresponding displays 77, 78 and 79 are shown. In an alternative implementation shown in dotted lines in FIG. 4, the outputs of the low-pass filter block 65 and the AM demodulator block 67 are connected to the inputs of amplifier and display driver blocks 81 and 82, respectively. The amplifier and display driver blocks 81 and 82 are further connected to the displays 79 and 78, respectively. Consequently, in this alternative implementation in which the amplifier and display driver blocks 74 and 75 are omitted, the apparatus is alternatively adapted to display the partial pressure of oxygen, the respiration rate and the heart rate at the displays 77, 78 and 79, respectively.

EXAMPLE

In a preferred embodiment of the electrode assembly according to the invention shown in FIG. 3 and comprising an electrode device 10 according to the invention, the metallic body 13 of the electrode device 10 was a silver body having chlorinated lower surface and an outer diametre of 9 mm. The pH-glass electrode 31 was arranged in a 4.5 mm hole of the silver body and comprised a main tube made of lead glass and a glass-membrane melted onto the main tube. Within the pH-glass electrode an interior electrolyte solution and an inner conductor or reference electrode 32 were arranged. The interior electrolyte solution was of the type described in published European Patent Application, publication no. 0 061 190, and had a composition of: 0.5M phenylphosphonic acid, 0.75M NaOH, and 0.01M NaCl. pH=6.84 (25° C.). The reference electrode 32 of the pH-glass electrode was a silver conductor of a thickness of 0.25 mm immersed in the interior electrolyte solution of the pH-glass electrode. The cathode wire 34 was a 25 μm platinum wire embedded within a glass tube 33 made of lead glass having an outer diametre of 1.4 mm. The O-ring 15 was a neoprene O-ring, and the electrode housing was an acrylonitrile-butadiene-styrene (ABS) electrode housing of Radiometer type. The fixation ring was an acrylonitrile-butadiene-styrene (ABS) ring of Radiometer type, described in U.S. Pat. No. 4,274,418. The membrane was of the construction described in the published Danish patent application No. 3170/82, and consisted of a basic membrane layer made of polytetrafluorethylene (PTFE) of a thickness of 12 μm and of an oxygen diffusion restricting inner layer of polypropylene of a thickness of 15 82 m in which an aperture corresponding to the exposed outer surface area of the pH-glass electrode, i.e. an aperture of a diametre of 4.5 mm was provided. The elecrolyte solution had a composition of 41 per cent propyleneglycol (1,2-propanediol), 42.5 per cent glycerine (1,2,3-propanetriol), 16.5 per cent water, and $KHCO_3/KCl$ 20/200 mmol/liter; all the above percentages are by weight. The Zener diode 23 had a Zener voltage $V_{ZE}=12$ V and the NTC resistor was a 5.6 kΩ NTC-resistor. The interior casting 27 was an epoxy casting. In the electrode device 40, the metallic ring 41 was made of an Ag-wire of a diametre of 0.9 mm. The thermistor 44 was an NTC resistor of the above type, i.e. a 5.6 kΩ NTC-resistor. The termistor supporting part 43 was an epoxy resin casting partially encasing the thermistor 44 and had an outer diametre of 6 mm and a thickness of 1 mm. The inner space 48 of the electrode device 40 was filled with air. The electrically conductive contact liquid 19 and 20 was of the composition propyleneglycol (1,2-propanediol), 50 per cent water and $KCl/KNO_3$ type 200/200 mmol/liter; all the above percentages are by weight.

In a test setup, the electrode assembly described in the above example and shown in FIG. 3, was connected to a conventional measuring apparatus comprising a $TCpO_2$ and $TCpCO_2$ monitor of the type Radiometer TCM 222 and an respiration and heart frequency measuring apparatus from the company Hewlett-Packard comprising a main frame of the type HP 78201, a respiration rate module of the type HP 78202B and a heart beat frequency module of the type HP 78203A through appropriate junction or branching boxes.

Figure 6:
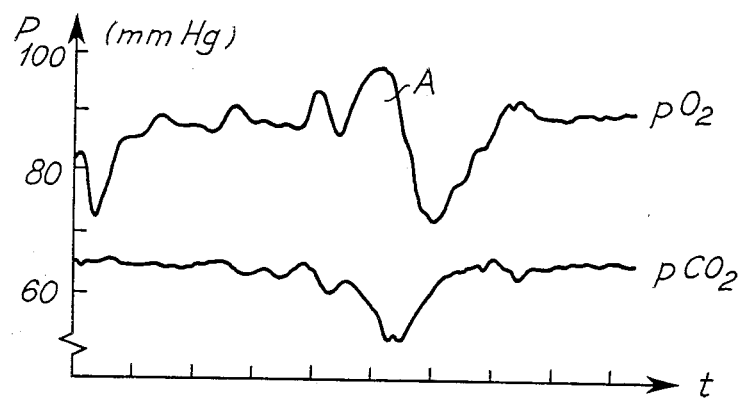

In FIG. 6, two diagrams are shown, which were recorded by means of the Radiometer TCM 222 monitor in the above described setup. The upper diagram illustrates a $pO_2$ response, and the lower diagram illustrate a $pCO_2$ response of a test person to the thorrax of whom the electrodes 10 and 40 were fixed. The responses were recorded simultaneously, and the diagrams are compensated as to pen offset. The unit of the abcissa-axis corresponds to a two minute time interval, and the total range of the ordinate axis is 100 mm Hg. From FIG. 6 it is evident that the $pO_2$ and the $pCO_2$ measuring electrode systems of the electrode device stabilize within a few minutes, and that the $pO_2$ and the $pCO_2$ measuring electrode systems respond homogeniously as the radical increase at A in the $pO_2$ response caused by hyperventilation of the test person is unambiguously followed by a decrease in the $pC_2$ response.

Figure 7:
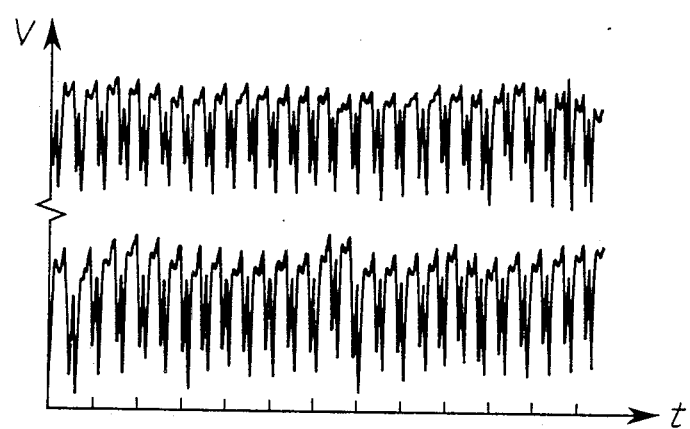
Figure 8:
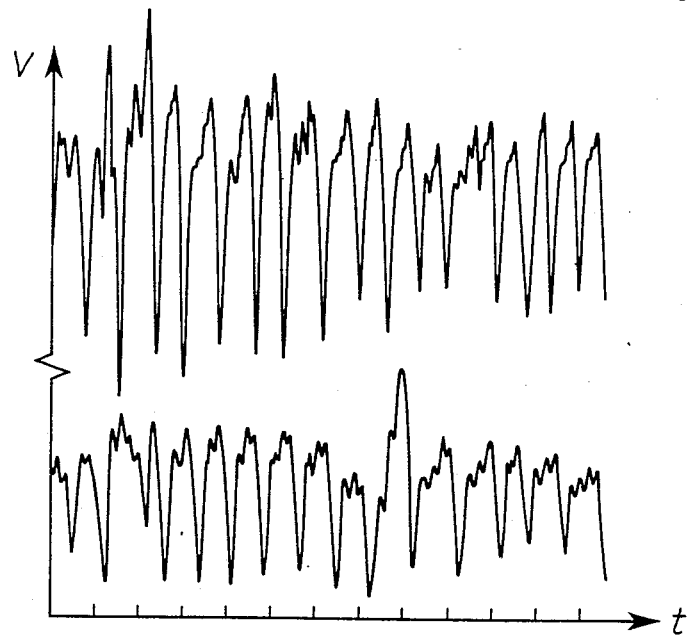

In FIGS. 7 and 8, response curves of the bioelectrical signal sensing electrodes of the electrode assembly of the type described in the above example and shown in FIG. 3 are compared to responses obtained by means of conventional bioelectrical signal sensing electrodes normally employed in connection with the above described HP respiration rate and heart beat frequency measuring apparatus. In FIG. 7, the upper response is an ECG (Electrocardiography) response of the bioelectrical signal sensing electrodes of the electrode assembly according to the invention recorded by means of the HP 78203A heart beat frequency module, and the lower response is an ECG response recorded by means of the conventional bioelectrical signal sensing electrodes connected to the HP 78203A measuring module. The unit of the abscissa-axis indicated in FIG. 7 corresponds to a time period of 2 sec. As is evident from FIG. 7, the two responses are basically identical to one another, and it is concluded that the bioelectrical signal measuring electrode system of the electrode assembly according to the invention has a response characteristic basically identical to the response characteristic of the conventional bioelectrical signal measuring electrode system. Furthermore, the losses of the bioelectrical signal measuring electrode system of the electrode assembly according to the invention is of the same order of magnitude as the losses of the conventional electrode system.

In FIG. 8, two curves are shown. The upper curve illustrates the TTI (transthoracal impedance) response recorded by means of the bioelectrical signal measuring electrode system of the above described electrode assembly according to the invention by employing the above respiration rate module HP 78202B. The lower curve illustrates the response recorded by employing conventional bioelectrical signal sensing electrodes connected to the HP 78202B respiration module. The unit of the abcissa-axis is also of the order of 2 sec. It is evident from FIG. 8 that the responses are basically identical to one another, i.e. the characteristics of the bioelectrical signal measuring electrode systems are identical to one another.

Although the invention has been described with reference to specific embodiments, it is to be understood that several modifications may be carried out within the scope of the present invention. Thus, techniques such as thin-film or thick-film technique, as described in GB Pat. No. 2.073.891 may be employed for providing the electrode device according to the invention or for providing components thereto Furthermore, the transmission from the electrode devices of the electrode assembly to the measuring apparatus may be carried out in a multiplexed state in accordance with the principles described in the patent applications claiming priority from the Danish patent application No. 2327/83. The electrode device according to the invention may further comprise a compensation electrode of the kind described in International Patent Application No. PCT/DK81/00035, publication no. WO81/02831.

REFERENCES

1. "Medical instrumentation application and design", John G. Webster, Houghton Mifflin Company, Boston © 1978.
2. "Self heated thermistors for thermal property measurement", J. W. Valvano, Procedings of the 35th annual conference on engineering in medicine and biology, 1982, Philadelphia, Pennsylvania, Vol. 24.

We claim:

1. An electrode device to be arranged at a skin surface part of a test person or a test object for transcutaneously measuring a blood gas parameter and for sensing a bioelectrical signal of said test person or test object, comprising:
   (a) a housing;
   (b) an electrochemical measuring electrode system for measuring said blood gas parameter and comprising:
      (i) at least two electrochemical electrodes for generating at least one measuring signal, said electrochemical electrodes being arranged in said housing electrically insulated in relation to one another, and
      (ii) an electrolyte;
   (c) a membrane permeable to said blood gas and to be arranged adjacent to said skin surface part so as to allow diffusion of said blood gas from said skin surface part through said membrane, said membrane being arranged in relation to said electrochemical electrodes so as to define an electrolyte chamber in front of said electrochemical electrodes, in which chamber said electrolyte is confined electrolytically communicating with said electrochemical electrodes;
   (d) an electrode for sensing said bioelectrical signal; and
   (e) means for transmitting said measuring signal and for transmitting said bioelectrical signal,
   said bioelectrical signal sensing electrode being constituted by one of said electrochemical electrodes of said electrochemical electrode system, said membrane further being arranged in relation to said electrochemical electrodes so as to separate said one electrode into a first part and a second part, said first part being covered by said membrane, and said second part being uncovered by said membrane so as to electrically conductively communicate with said skin surface part when said membrane is arranged adjacent thereto.

2. An electrode device according to claim 1, further comprising an electrically conductive contact liquid electrically contacting said second part of said one electrode and said skin surface part when said membrane is arranged adjacent to said skin surface part, such that said second part of said one electrode electrically conductively communicates with said skin surface part.

3. An electrode device according to claim 2, said second part of said one electrode being recessed in relation to said first part of said one electrode.

4. An electrode device according to claim 2, further comprising a fastening means for fastening said housing to said skin surface part.

5. An electrode device according to claim 4, said fastening means being a separate fastening component of an annular configuration for receiving said housing and, together with said membrane, defining a contact liquid chamber.

6. An electrode device according to claim 1, said electrochemical measuring electrode system comprising a potentiometric electrode system including a reference electrode and a pH-sensitive electrode, said reference electrode further constituting said bioelectrical signal measuring electrode.

7. An electrode device according to claim 6, said reference electrode being a silver reference electrode, and said pH-sensitive electrode being a pH-glass electrode.

8. An electrode device according to claim 1, said electrochemical measuring electrode system comprising a polarographic sensing electrode system including an anode and a cathode, said anode further constituting said bioelectrical signal measuring electrode.

9. An electrode device according to claim 8, said anode being a silver anode, and said cathode being a noble metal cathode.

10. An electrode device according to claim 1, further comprising a second bioelectrical signal sensing electrode, said second bioelectrical signal sensing electrode being constituted by a separate metallic body, said separate metallic body being electrically insulated in relation to said one electrode and having an exposed surface part.

11. An electrode device according to claim 10, said metallic body constituting said second bioelectrical signal sensing electrode being a part of said housing.

12. An electrode device according to claim 9, further comprising a potentiometric electrode system including a reference electrode and a pH-sensitive electrode, said silver anode of said polarographic electrode system further constituting said reference electrode of said potentiometric electrode system.

13. An electrode assembly comprising:
(1) a first electrode device to be arranged at a first skin surface part of a test person or test object for transcutaneously measuring a blood gas parameter and for sensing a first bioelectrical signal, comprising:
  (a) a housing;
  (b) an electrochemical measuring electrode system for measuring said blood gas parameter and comprising:
    (i) at least two electrochemical electrodes for generating at least one measuring signal, said electrochemical electrodes being arranged in said housing electrically insulated in relation to one another; and
    (ii) an electrolyte;
  (c) a membrane permeable to said blood gas and to be arranged adjacent to said first skin surface part so as to allow diffusion of said blood gas from said first skin surface part through said membrane, said membrane being arranged in relation to said electrochemical electrodes so as to define an electrolyte chamber in front of said electrochemical electrodes, in which chamber said electrolyte is confined electrolytically communicating with said electrochemical electrodes;
  (d) an electrode for sensing said first bioelectrical signal; and
said bioelectrical signal sensing electrode being constituted by one of said electrochemical electrodes of said electrochemical electrode system, said membrane further being arranged in relation to said electrochemical electrodes so as to separate said one electrode into a first part and a second part, said first part being covered by said membrane, and said second part being uncovered by said membrane so as to electrically conductively communicate with said first skin surface part when said membrane is arranged adjacent thereto; and (2) a second electrode device to be arranged adjacent to a second skin surface part of said test person or test object and for sensing a second bioelectrical signal of said test person or test object, comprising:
  (a) a housing;
  (b) an electrode for sensing said second bioelectrical signal, said bioelectrical signal sensing electrode being arranged in said housing, being electrically insulated therefrom, and being adapted to electrically conductively communicate with said second skin surface part when said second electrode device is arranged adjacent to said second skin surface part; and
(3) means for transmitting said measuring signal, said first bioelectrical signal, and said second bioelectrical signal to a measuring apparatus;
said bioelectrical signal sensing electrodes of said first and second electrode devices being adapted to cooperate with said measuring apparatus through said means for transmitting said first and second bioelectrical signals.

14. An electrode assembly according to claim 13, further comprising a junction, said means for transmitting said first bioelectrical signal of said first electrode device and said means for transmitting said second bioelectrical signal of said second electrode device being connected to said junction for joint connection to said measuring apparatus.

15. An electrode assembly according to claim 14, said second electrode device further comprising an electrically conductive contact liquid electrically contacting said bioelectrical signal sensing electrode of said second electrode device and said second skin surface part when said second electrode device is arranged adjacent said second skin surface part such that said second electrode device electrically communicates with said second skin surface part.

16. An electrode assembly according to claim 15, said housing of said second electrode device defining a front surface part, and said bioelectrical signal sensing electrode of said second electrode device being recessed in relation to said front surface part of said housing of said second electrode device.

17. An electrode assembly according to claim 16, said bioelectrical signal sensing electrode of said second electrode device being a silver electrode.

18. An electrode assembly according to claim 14, said second electrode device further comprising a fastening means for fastening said housing of said second electrode device to said second skin surface part.

19. An electrode assembly according to claim 18, said fastening means of said second electrode device being a separate fastening component of an annular configuration for receiving said housing of said second electrode device and, together with said second bioelectrical signal sensing electrode of said second electrode device, defining a contact liquid chamber.

20. An electrode assembly according to claim 19, wherein said first electrode device further comprises a fastening means for fastening said housing of said first electrode device to said first skin surface part, said fastening means being a separate fastening component of an annular configuration for receiving said housing and, together with said membrane, defining a contact liquid chamber; and said separate fastening components of said first electrode device and said separate fastening component of said second electrode device being adapted to further enable interchanging of said first and second electrode devices in relation to said fastening components.

21. An electrode assembly according to claim 13, said second electrode device further comprising a temperature sensing means, said temperature sensing means thermally conductively communicating with said second skin surface part for sensing the temperature thereof when said second electrode device is arranged adjacent to said second skin surface part.

* * * * *